(12) United States Patent
Aberl et al.

(10) Patent No.: US 8,647,890 B2
(45) Date of Patent: *Feb. 11, 2014

(54) METHOD FOR THE RAPID DIAGNOSIS OF TARGETS IN HUMAN BODY FLUIDS USING UNDILUTED SAMPLES

(75) Inventors: Franz Aberl, Kranzberg (DE); Marcus Scheibenzuber, München (DE); Robert P. Sambursky, Bradenton, FL (US); Robert W. VanDine, Montoursville, PA (US); Jose S. Sambursky, Johnson City, NY (US)

(73) Assignee: Rapid Pathogen Screening, Inc., Sarasota, FL (US)

(*) Notice: Subject to any disclaimer, the term of this patent is extended or adjusted under 35 U.S.C. 154(b) by 260 days.

This patent is subject to a terminal disclaimer.

(21) Appl. No.: 12/701,799

(22) Filed: Feb. 8, 2010

(65) Prior Publication Data
US 2010/0143891 A1 Jun. 10, 2010

Related U.S. Application Data

(62) Division of application No. 11/698,053, filed on Jan. 26, 2007, now abandoned, and a division of application No. 11/052,748, filed on Feb. 9, 2005, now Pat. No. 7,723,124.

(60) Provisional application No. 60/542,303, filed on Feb. 9, 2004.

(51) Int. Cl.
*G01N 33/558* (2006.01)
*G01N 33/53* (2006.01)

(52) U.S. Cl.
USPC .................................. 436/514; 435/7.1

(58) Field of Classification Search
USPC ............... 436/514; 435/4, 7.1, 287.1, 287.2, 435/287.7
See application file for complete search history.

(56) References Cited

U.S. PATENT DOCUMENTS

| 4,094,647 A | 6/1978 | Deutsch et al. |
| 4,299,916 A | 11/1981 | Litman et al. |
| 4,737,456 A | 4/1988 | Weng et al. |
| 4,844,866 A | 7/1989 | Wallace et al. |
| 4,857,453 A | 8/1989 | Ullman et al. |
| 4,904,448 A | 2/1990 | Kawahara |

(Continued)

FOREIGN PATENT DOCUMENTS

| DE | 19622503 C2 | 7/1998 |
| EP | 0306772 A1 | 3/1989 |

(Continued)

OTHER PUBLICATIONS

Toraason, Mark; Sussman, Gordon; Biagini, Raymond; Meade, Jean; Beezhold, Donald; and Dori Germolec. "Latex Allergy in the Workplace," Toxicological Sciences. 58 (2000) 5-14.

(Continued)

*Primary Examiner* — Shafiqul Haq
*Assistant Examiner* — Gary E. Hollinden
(74) *Attorney, Agent, or Firm* — Brown & Michaels, PC

(57) ABSTRACT

More particularly, the present invention relates to a method for the detection of a target, e.g. pathogen in a human body fluid wherein a body fluid sample is collected with a swab member.

27 Claims, 4 Drawing Sheets

(56) References Cited

U.S. PATENT DOCUMENTS

| | | |
|---|---|---|
| 4,960,691 A | 10/1990 | Gordon et al. |
| 4,963,325 A | 10/1990 | Lennon et al. |
| 4,968,633 A | 11/1990 | Marcucci |
| 4,981,786 A * | 1/1991 | Dafforn et al. ............... 435/7.92 |
| 5,075,078 A | 12/1991 | Osikowicz et al. |
| 5,120,643 A | 6/1992 | Ching et al. |
| 5,451,504 A | 9/1995 | Fitzpatrick et al. |
| 5,591,645 A | 1/1997 | Rosenstein |
| 5,607,863 A * | 3/1997 | Chandler ..................... 436/518 |
| 5,714,341 A | 2/1998 | Thieme et al. |
| 5,714,389 A | 2/1998 | Charlton et al. |
| 5,798,273 A | 8/1998 | Shuler et al. |
| 5,869,345 A | 2/1999 | Chandler |
| 5,989,921 A | 11/1999 | Charlton et al. |
| 5,998,220 A | 12/1999 | Chandler |
| 6,017,767 A | 1/2000 | Chandler |
| 6,046,058 A | 4/2000 | Sun |
| 6,087,184 A | 7/2000 | Magginetti et al. |
| 6,168,956 B1 | 1/2001 | Chandler |
| 6,187,598 B1 | 2/2001 | May et al. |
| 6,221,678 B1 | 4/2001 | Chandler |
| 6,235,539 B1 | 5/2001 | Carpenter |
| 6,375,896 B1 | 4/2002 | Wuske et al. |
| 6,485,982 B1 | 11/2002 | Charlton |
| 6,498,010 B1 | 12/2002 | Fitzgerald et al. |
| 6,514,773 B1 | 2/2003 | Klein et al. |
| 6,548,309 B1 | 4/2003 | Moore et al. |
| 6,555,390 B2 | 4/2003 | Chandler |
| 6,565,808 B2 * | 5/2003 | Hudak et al. .................. 422/411 |
| RE38,430 E | 2/2004 | Rosenstein |
| 6,703,196 B1 | 3/2004 | Klepp et al. |
| 6,716,641 B1 | 4/2004 | Sundrehagen |
| 6,737,278 B1 | 5/2004 | Carlsson et al. |
| 6,890,484 B2 | 5/2005 | Bautista et al. |
| 6,893,880 B2 | 5/2005 | Carpenter |
| 6,979,576 B1 * | 12/2005 | Cheng et al. ................. 435/7.32 |
| 7,109,042 B2 | 9/2006 | May et al. |
| 7,267,992 B2 | 9/2007 | Goerlach-Graw et al. |
| 7,300,750 B2 | 11/2007 | Smart et al. |
| 7,393,697 B2 | 7/2008 | Charlton |
| 7,459,125 B1 * | 12/2008 | Stankov et al. ............... 422/412 |
| 7,704,729 B2 * | 4/2010 | Chandler .................... 435/287.1 |
| 7,723,124 B2 * | 5/2010 | Aberl et al. ................... 436/518 |
| 7,939,342 B2 | 5/2011 | Song et al. |
| 2002/0036170 A1 | 3/2002 | Harvey et al. |
| 2003/0049658 A1 | 3/2003 | Smart et al. |
| 2003/0119083 A1 | 6/2003 | Owens et al. |
| 2003/0232451 A1 | 12/2003 | Casterlin et al. |
| 2004/0082077 A1 | 4/2004 | Hu |
| 2004/0115831 A1 | 6/2004 | Meathrel et al. |
| 2004/0152142 A1 | 8/2004 | Klepp et al. |
| 2004/0161857 A1 | 8/2004 | Yugawa et al. |
| 2004/0235189 A1 | 11/2004 | Lu |
| 2005/0142622 A1 | 6/2005 | Sanders et al. |
| 2005/0148097 A1 | 7/2005 | Mizukami |
| 2005/0181517 A1 | 8/2005 | Chandler et al. |
| 2005/0244986 A1 | 11/2005 | May et al. |
| 2006/0003390 A1 | 1/2006 | Schaffler et al. |
| 2006/0024767 A1 | 2/2006 | Hajizadeh et al. |
| 2006/0121626 A1 | 6/2006 | Imrich |
| 2006/0134802 A1 * | 6/2006 | Donati et al. ................. 436/514 |
| 2006/0172434 A1 | 8/2006 | Rowell |
| 2010/0112725 A1 * | 5/2010 | Babu et al. .................... 436/518 |
| 2010/0297611 A1 * | 11/2010 | Sambursky et al. ............. 435/5 |

FOREIGN PATENT DOCUMENTS

| | | | |
|---|---|---|---|
| EP | 0699906 A2 | 3/1996 | |
| EP | 0811847 * | 6/1997 | .......... G01N 33/558 |
| JP | 63501074 A | 4/1988 | |
| JP | 9171019 A | 6/1997 | |
| JP | 10-132820 A | 5/1998 | |
| JP | 2002340897 A | 11/2002 | |
| JP | 2002539425 T | 11/2002 | |
| JP | 2005529305 A | 9/2005 | |
| WO | 9415215 A1 | 7/1994 | |
| WO | 9936776 A1 | 7/1999 | |
| WO | 9960402 A1 | 11/1999 | |
| WO | 0054024 A1 | 9/2000 | |
| WO | 0136975 A1 | 5/2001 | |

OTHER PUBLICATIONS

Wambura, et al., "Diagnosis of Rinderpest in Tanzania by a Rapid Chromatographic Strip-test," Tropical Animal Health and Production, vol. 32, No. 3, Jun. 2000, pp. 141-145.

Uchio, et al., "Rapid Diagnosis of Adenoviral Conjunctivitis on Conjunctival Swabs by 10-Minute Immunochromatography," vol. 104, No. 8, Aug. 1997, pp. 1294-1299.

Sobanski et al., "Detection of adenovirus and rotavirus antigens by an immuno-gold lateral flow test and ultrasound-enhanced latex agglutination assay", Journal of Medical Microbiology, 50, 203 (2001).

Bruning et al., "A rapid chromatographic strip test for the pen-side diagnosis of rinderpest virus," Journal of Virological Methods 81 (1999) 143-154.

Sambursky, "501-K Summary of Safety and Effectiveness" (Sep. 14, 2005).

RPS/Rapid Pathogen Screening—About RPS, http://web.archive.org/web/20051226105022/rps-tests.com/about.html, Dec. 26, 2005.

Kent, ed., "Point-of-Care Screening for Conjunctivitis", Review of Ophthalmology, vol. 12, Iss. 4, http://www.revophth.com/index.asp?page=1_707.htm (Apr. 15, 2005).

Sambursky et al., "The RPS Adeno Detector for Diagnosing Adenoviral Conjunctivitis", Ophthalmology, vol. 113, No. 10, pp. 1758-1764 (Oct. 2006).

Udeh et al., "Cost Effectiveness of a Point-of-Care Test for Adenoviral Conjunctivitis", The American Journal of the Medical Sciences, vol. 336, No. 3, pp. 254-264 (Sep. 2008).

Sambursky, "Physicians Guide to RPS Adeno Detector™", http://www.eyecaresource.com/conditions/pink-eye/physician-guide.html, Jun. 3, 2009.

"American Medical Association Clears Path for Adenoviral Conjunctivitis"Pink Eye"Detector," Medical News Today, Nov. 8, 2007, http://www.medicalnewstoday.com/articles/88067.php.

"Rapid test for pink eye may curb overuse of antibiotics", http://www.stjohns.com/news/pinkeyetest.aspx (Jan. 26, 2009).

QuickVue Chlamydia Test, pp. 1-14, Quidel, Jan. 2006 (Exhibit A).

Binax Now Package Insert, Inverness Medical, Rev. 4, Sep. 9, 2009 (Exhibit B).

Rapid Response Strep A, BTNX, Inc., Rev03-08092006 (Exhibit C).

* cited by examiner

METHOD FOR THE RAPID DIAGNOSIS OF TARGETS IN HUMAN BODY FLUIDS USING UNDILUTED SAMPLES

REFERENCE TO RELATED APPLICATIONS

This is a divisional patent application of copending application Ser. No. 11/698,053, filed Jan. 26, 2007, entitled "Method for the Rapid Diagnosis of Targets in Human Body Fluids" and copending application Ser. No. 11/052,748, filed Feb. 9, 2005, entitled "Method for the Rapid Diagnosis of Targets in Human Body Fluids", which claimed one or more inventions which were disclosed in U.S. Provisional Application No. 60/542,303, filed Feb. 9, 2004, entitled "Method for the Rapid Diagnosis of Targets in Human Body Fluids". The benefit under 35 USC §119(e) of the United States provisional application is hereby claimed, and the aforementioned applications are hereby incorporated herein by reference.

TECHNICAL FIELD OF THE INVENTION

The present invention relates to a method for the detection of targets, e.g. pathogens and/or allergy-associated components in a human body fluid wherein a body fluid sample is collected with a swab member. The samples are transferred from the swab member to a sample analysis device, on which an analysis of the targets, e.g. by immunochemical or enzymatic means can take place. The test result may be displayed within a short period of time and can be directly read out by the user. Further, a test kit for carrying out the method of the invention is provided.

BACKGROUND OF THE INVENTION

Rapid, point-of-care analysis is becoming increasingly important in the diagnosis and treatment of various viral and other pathogenic microbiological agents (bacteria, others). Especially in the acute status of a infectious disease medical doctors have a need for immediate detection of the causal agent for the symptoms observed.

Prior art discloses a rapid assay for HIV specific antibodies in saliva samples. A saliva sample is gained by means of a sampling stick. The saliva sample is diluted in a sample buffer and a lateral flow immunoassay is dipped into the diluted saliva sample [U.S. Pat. No. 5,714,341].

German Patent Nr. DE19622503 suggests to apply lateral flow immunoassays for the detection of illegal narcotics in saliva or sweat.

Conjunctivitis, commonly known as red eye or pink eye, may be caused by several different agents including viruses, bacteria and allergens. Different etiologies require different treatments. Infectious conjunctivitis is typically contagious. Conjunctivitis is generally diagnosed clinically, by gross examination, and (during a routine eye exam) slit lamp biomicroscopy. This method does not provide information on the specific infectious agent. If specific (pathogen typing) diagnosis is necessary, swabs of the inferior formix are sent for laboratory analysis to determine the type of pathogen. The preferred methods for laboratory analysis are cell culture with confirmatory direct immunofluorescence, ELISA or PCR. The disadvantage of this diagnostic strategy is that laboratory analysis needs typically between two and ten days, utilizes complex diagnostic equipment, and may require technical skill in both performing and interpreting results. This time period is problematic for a proper treatment of potentially infectious forms of conjunctivitis that cannot be specifically classified/connected with a certain pathogenic agent.

A publication by Uchio et al. (Opthalmology 104 (1997), 1294-1299) discloses a method for the detection of adenovirus in eye fluid specimens. The method comprises collecting a sample of eye fluid and detecting the analyte on a paper disc by enzyme immunoadsorption. The detection, however, lacks specificity and sensitivity.

Thus, it is the objective of the invention to provide a sensitive and rapid non-invasive method for the detection of pathogens, e.g. bacterial or viral infectious agents in body fluids.

SUMMARY OF THE INVENTION

In a first aspect, the present invention relates to a method for the detection of a target which is selected from pathogens and/or allergy-associated components in a body fluid comprising the steps:
(a) non-invasively collecting a body fluid sample with a swab member,
(b) transferring the sample to a application zone on a sample analysis device and
(c) analysing the sample.

In a further aspect, the invention relates to a method for diagnosing conjunctivitis comprising the steps:
(a) non-invasively collecting an eye fluid sample with a swab member,
(b) transferring the sample to a application zone on a sample analysis device and
(c) analysing the sample.

In still a further aspect, the invention relates to a test kit comprising
(a) a swab member for non-invasively collecting a body fluid sample,
(b) a sample analysis device comprising a detection zone, wherein the detection zone contains reagents for determining the presence and/or amount of at least one target which is selected from pathogens and/or allergy-associated components.

In still a further aspect, the invention relates to a test kit comprising
(a) a swab member for non-invasively collecting an eye fluid sample,
(b) a sample analysis device comprising a detection zone, wherein the detection zone contains reagents for determining the presence and/or amount of at least one target which is selected from pathogens and/or allergy-associated components wherein the target is a causative agent or mediator of conjunctivitis or a plurality of such causative agents and/or mediators.

DETAILED DESCRIPTION OF PREFERRED EMBODIMENTS

Figure 1:
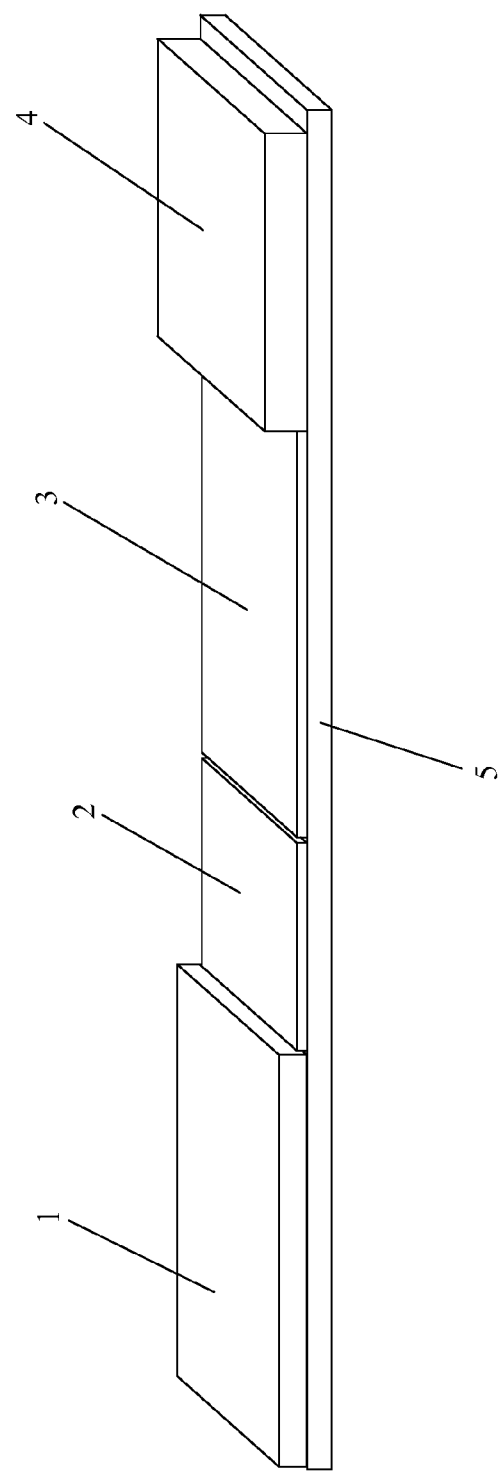
FIG. 1 shows a sample analysis device in the form of a chromatographic test strip comprising a plurality of different strip materials building an absorbent pad (1), an application zone (2), a detection zone (3) and a waste zone (4). The strip materials are arranged on an adhesive plastic backing (5). The absorbent pad (1) is providing for adding an elution medium in order to facilitate the transfer of the sample to the detection zone (3).
Figure 2:
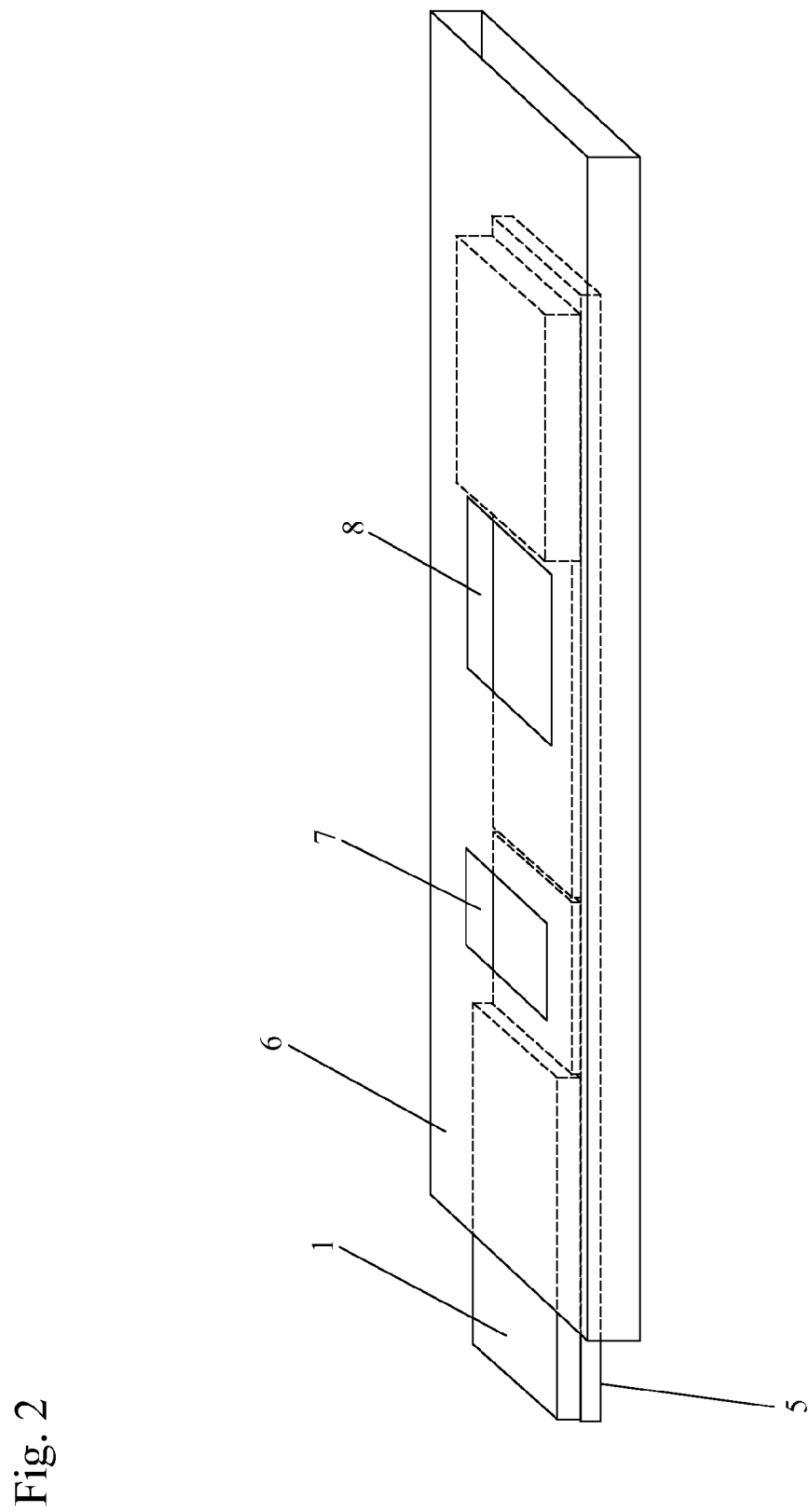
FIG. 2 shows a plastic housing (6) containing the strip as shown in FIG. 1. A sample application window (7) is provided for bringing a swab member into contact with the strip. The test result is displayed in the read out window (8).

The invention provides a sensitive and rapid method for the detection of targets, e.g. pathogens and/or allergy-associated components in samples collected by non-invasive means from a body fluid. The pathogens are selected from viruses, microorganisms, e.g. bacteria and parasites, e.g. amoebae or nematodes. The allergy-associated components are selected from allergens and anti-allergic components. The detection may comprise a direct detection of the target, e.g. the pathogen and/or the detection of antibodies against the target, e.g. the pathogen which are present in the fluid sample to be tested. Preferably, the method comprises a parallel determination of a plurality of targets.

The body fluid is preferably a fluid from a body surface selected from mucose membrane fluids (of the oral, nasal, vaginal, and ocular cavities) tears, secretions from glands and secretions from lesions or blisters, e.g. lesions or blisters on the skin. More preferably, the sample is selected from oral, nasal, ocular, genital and rectal fluids and secretions from skin lesions or blisters. Most preferably, the sample is an eye fluid. A significant advantage of the method is that results are provided within the medical consultation period, e.g. in few minutes. Preferably, the results are provided in a time period up to 20 minutes, more preferably up to 15 minutes. Also, as the test is noninvasive, it poses very little risk to the patient. Thus the best available treatment can be applied on a timely basis for a specific pathogen. A further advantage over prior art methods is that only a few microliters of sample are required to perform an analysis. The sample is preferably about 0.1 µl to about 100 µl, more preferably about 0.2 µl to about 20 µl and most preferably about 0.5 µl to about 10 µl.

The invention may be performed by means of a simple test kit. Handling of the test kit does not necessitate additional laboratory equipment, further handling of reagents or instrumentation. Another important advantage of the invention described below is that the detection limit is typically 10 to 100 times lower than currently available diagnostic tests because samples do not require dilution before they are transferred to the analysis device. Therefore the disclosed method has proven to be more sensitive and accurate than methods of the prior art.

The invention discloses a non-invasive method for the rapid and point-of-care determination of pathogens from body fluids. The method is suitable for diagnosis in human beings and animals, e.g. pets or livestock animals. A preferred application is the detection of pathogens in eye fluid, e.g. human eye fluid. In this embodiment the pathogen to be detected is a causative agent of conjunctivitis or a plurality of such causative agents. For example, the pathogen is selected from the group of adenoviruses, herpesviruses, chlamydiae, cytomegaloviruses and combinations thereof. More preferably, a plurality of pathogens are detected on a single sample analysis device. For example, the sample analysis device may allow a simultaneous detection of a plurality of pathogens, particularly of at least two, of at least three, of at least four or of at least five pathogens selected from the group consisting of adenoviruses, herpesviruses, chlamydiae, cytomegaloviruses, pseudomonas, streptococci, haemophilus, staphylococci, amoebae, particularly Acanthamoeba and nematodes, particularly Onchocera volvulus. More preferably, the method comprises a simultaneous detection of adenoviruses, herpesviruses, chlamydiae, cytomegaloviruses and Acanthamoeba.

In addition the invention provides a non-invasive method for the rapid and point-of-care determination of at least one allergy-associated component, particularly an allergen (e.g. pollen, dust, etc.) and/or an antiallergen, particularly a component which is produced in the body in response to an allergenic challenge (e.g. IgE, histamine, etc.), in a body fluid as described above. More particularly, the invention relates to methods and devices for the diagnosis of allergy-associated components in eye fluid, e.g. human eye fluid. In a preferred embodiment, the determination of at least one allergy-associated component may be combined with the determination of at least one pathogen as described above.

In the method of the invention, a body fluid sample is non-invasively collected with a collection device or swab member, respectively. The collection step preferably comprises wiping or dabbing the swab member over a surface of the body containing body fluid to be tested. Usually, the swab member is sterile. The swab member may be dry or pretreated with a fluid before the collection step. For example, using a gentle swirling motion, a sterile swab member may be applied to the body surface or mucous membrane of concern and allowed to capture any pathogens and/or allergy-associated components contained in the body fluid.

The swab member may be a part which is separate from the sample analysis device and the sample is transferred by contacting the sample analysis device with the swab member under conditions wherein at least a part of the sample on the swab member is transferred to the sample analysis device. In this embodiment, the swab member is preferably contacted with a sample application zone on the analysis device from which the sample is then transferred to the detection zone. The contact preferably comprises fixing the swab member in a contact position with the sample analysis device in which the sample collection zone of the swab member is in direct contact with the sample application zone of the analysis device. Thus, the swab member and/or the analysis device preferably comprises fixing means for providing a fixed contact between both parts in a predetermined position. Alternatively, the swab member may be an integrated part of the sample analysis device and the transfer comprises passing at least a part of the sample on the swab member to the detection zone on the sample analysis device.

The transfer of the sample from the swab member to the detection zone on the sample analysis device is preferably a direct transfer, i.e. the transfer takes place without pretreatment of the sample on the swab member. Preferably, the transfer comprises an elution of the sample from the swab member with an elution medium, e.g. a buffer or water. The elution medium may be added from an external source or may be provided e.g. as a reservoir within the analysis device. Further, the transfer is preferably a chromatographic and/or capillary transfer of fluid to the detection zone on the sample analysis device.

In a preferred embodiment, the sample analysis device comprises a chromatographic test strip, e.g. a lateral flow test strip. The sample analysis device may comprise a sample application zone, a detection zone, optionally a waste zone, optionally a carrier backing, optionally a housing and optionally an opening for result read out. The sample analysis in the detection zone may be carried out by standard means, e.g. by an immunological or enzymatic detection method. Preferably, the detection method comprises the use of test reagents capable of specifically binding the targets, e.g. pathogens to be tested or antibodies or other receptors against these targets, e.g. pathogens and subsequent visualisation of the bound entity, e.g. by enzymatic detection or by means of direct labelling groups, such as colloidal gold.

In an especially preferred embodiment, the swab member is placed on a lateral flow test strip. With this step the collected specimen is transferred directly on an immunochromatographic or enzymatic test strip. The test strip consists of one or several capillary active fleeces or membranes. The detection process will be either started directly with sample transfer or may require an elution medium to be applied for sample analysis. Preferably this elution medium is simple tap water. In the case of an immunochemical test strip, the chosen elution medium moves towards a detection zone and thereby passes the contact site within the collection device. The analyte is diluted by the elution medium and carried with it to the detection zone. In the detection zone the analyte is determined by qualitative and/or quantitative methods, e.g. in an immunological binding reaction.

The test strip can be made of one single chromatographic material, or preferably several capillary active materials made of the same or different materials and fixed on a carrier backing. These materials are in close contact with each other so as to form a transport path along which a liquid driven by capillary forces flows from the start zone, passing the contact site of the swab and the detection zone, towards a waste zone at the other end of the strip.

Furthermore this invention is disclosing a device and test kit for the performance of the described method.

In the method of invention, it is possible to make use of different immunological testing procedures to detect bacterial or viral constituents on one or several immunological binding reactions. In a preferred embodiment, a chromatography test strip contains:
   an application zone.
   a conjungate zone containing at least one labeled binding partner that is able to migrate with the elution medium. The binding partner is capable of specifically binding to an analyte and to a further specific reagent in the detection zone.
   a detection zone containing a first section for the detection of a first analyte, e.g. a test line, comprising an immobilized specific binding partner for the analyte, and optionally further sections for the detections of further analytes, and at least one control section, e.g. a control line comprising an immobilized specific binding partner of an indicator substance indicating the functionality of the test kit.

In a preferred embodiment, the specific binding partners for the analytes in the conjugate and the detection zone are monoclonal, polyclonal or recombinant antibodies or fragments of antibodies capable of binding to a pathogen. On the other hand, the specific binding partners may also be antigens capable of binding to antibodies against a pathogen or an allergen. Other types of binding partners are bioorganic macromolecules like aptamers or receptors. The conjugate zone may be located before, within or after the sample application zone, seen in the running direction of the eluent liquid. The test line(s) is(are) located after the conjugate/application zone and the control line(s) is(are) located after the test line. Together, the test line(s) and control line(s) comprise the detection zone.

Depending on the type of detection method, different binding partners are present in the different zones. In a sandwich immunoassay, it is preferred to have a labeled, non-immobilized analyte binding partner in the conjugate zone. The binding partner forms a complex with the analyte which is bound to the immobilized binding partner at the test line. In a preferred manner, the label of the conjugate binding partner is an optically detectable label. Forming a complex at the test line concentrates and immobilizes the label and the test line gets visible for the bare eye, indicating a positive test result. Particularly preferred are direct labels, and more particularly gold labels which can be best recognized by the bare eye. Additionally, an electronically photometrical read out device can be used to obtain more precise results and a semi-quantification of the analyte. Other labels may be latex, fluorophores or phosphorophores.

In order to test ocular fluids, a sample may be collected with a sample collection device from the patient's eye by a health care professional. The sample collection device should be wiped or dabbed slightly several times between in the inferior formix of the lower eye lid. If necessary the collection device may be wet with sterile physiological saline to decrease patient's discomfort. This procedure is well known in the opthalmology practice as it is necessary for collecting specimens for conventional laboratory analysis. Generally the sample collection device comprises a capillary active material suitable for receiving a body fluid sample. In a preferred manner the sample collection material is made out of fibers on the basis of cellulose, polyester, rayon or calcium alginate. However, the sample collection device can also be designed as a microengineered mechanical structure containing microcapillaries and/or microchannels.

Figure 4:
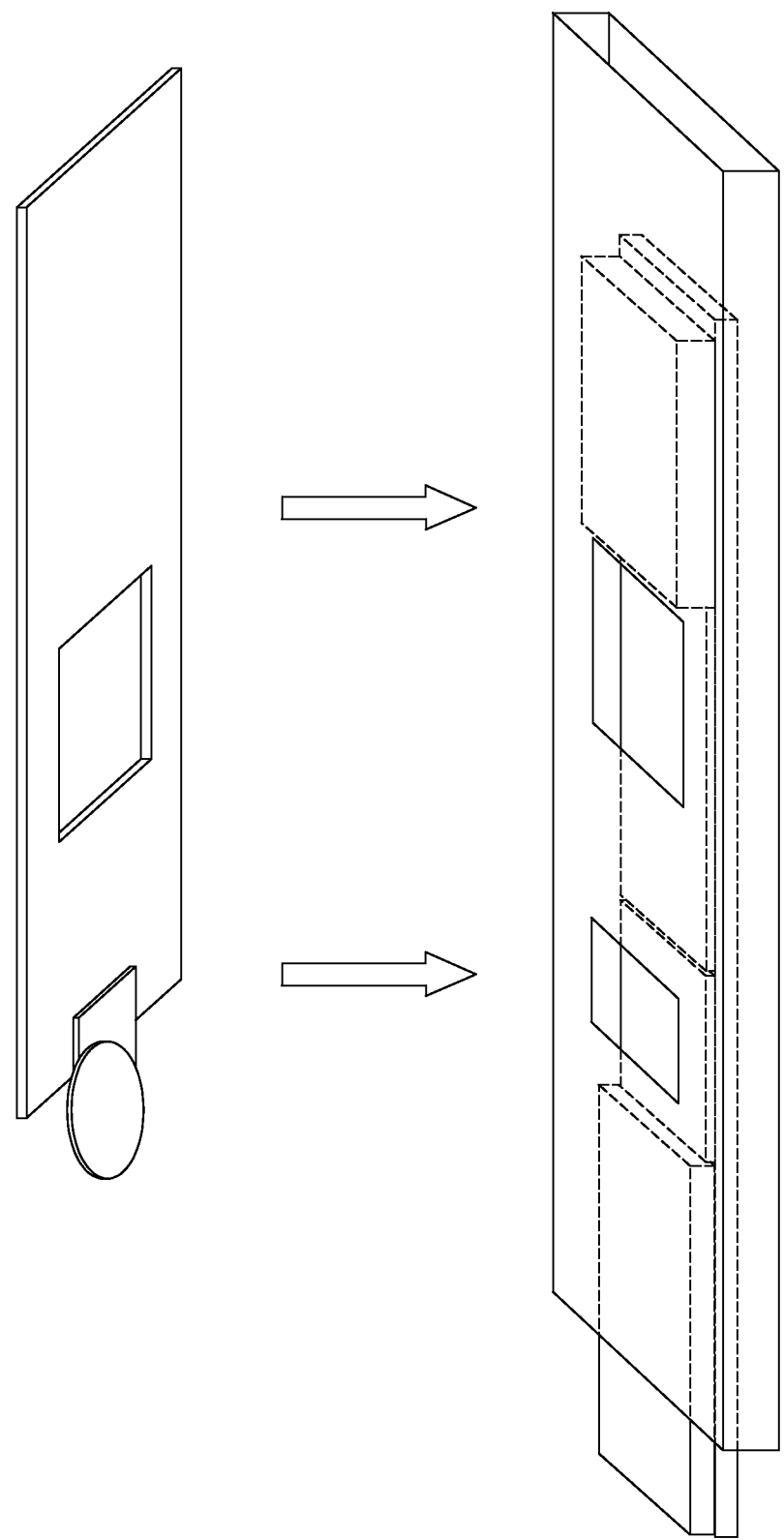
FIG. 4 shows a test kit comprising a sample analysis device according to FIGS. 1 and 2 and a swab member according to FIG. 3.

After the sample is collected, the collection device is fixed to the plastic housing containing the test strip (FIG. 4) and thereby the collection applicator is slightly pressed on the application zone of the strip. The collection device remains in this position.

In an alternative embodiment, the sample is taken by a standard swab member as currently used in the physician's office or emergency rooms. This swab member is subsequently pressed into the application zone of the chromatographic test strip by means of an additional device similar to the sample collection unit.

In another preferred embodiment, the sample is taken by a swab member and the sample collection devices is pressed for only a short time into the application zone of the chromatographic test strip. A short period of time preferably means a time up to 20 seconds, particularly between 0.1 and 10 seconds. A transfer of the sample is happening within the contact period.

In the next step, an elution medium is applied by dipping the absorbent pad into the chromatographic liquid. The absorbent pad is made of a particularly well-absorbing material which delivers the liquid for the immunochemical or enzymatic reactions. Preferred elution media are water or buffer solutions that are conventionally used in immunoassays.

Alternatively the elution medium is contained in a reservoir which may be integrated within the analysis device, e.g. as an ampoule or a blister. The reservoir may be opened by fixing the swab member or sample collection device on the detection part of the device or by additional means.

After a time period of up to 15 minutes, preferably within two to five minutes, the result can be read out in the detection zone. The result is considered positive when at least a partial area of the test line and the control line shows a color change.

EXAMPLE

Test kit for the detection of adenovirus from patient's eye swab

The structure of a test strip is depicted in FIG. 1.

The polyester fleece for the absorbent pad was manufactured by Binzer, Hatzfeld, Federal Republic of Germany. The fleece is a polyester fleece reinforced with 10% curalon. The thickness ranges 1 and 2 mm, the absorbance capacity is 1800 ml/m$^2$.

The application/conjugate zone consists of 80 parts polyester and 20 parts viscous staple fibers at a thickness of 0.32 mm and an absorbing capacity of 500 ml/m$^2$. The fleece is impregnated with the following solutions and then dried: 100 mmol/l HEPES Buffer, pH 7.5, 100 mol/l NaCl, conjugate of gold particles and anti-Hexon antibodies at a concentration that has an optical density of 10 at 520 nm. Hexon is a protein that is common in the capsid of human adenoviruses. The gold sol was manufactured according to standard procedures (Fres. Nature Vol. 241, p. 20-22, 1973). Conjugation with the antibody was carried out according to prior art procedure (J. Immunol. Meth. Vol. 34, p. 11-31, 1980). The sample application takes place in the application/conjugate zone.

The detection zone consists out of a nitrocellulose (NC) membrane with a nominal pore size of 8 µm and a thickness of 100 µm produced by Schleicher & Schuell, Germany. The test line contains a Hexon specific antibody (not labeled) which is specific for a different epitope than the antibody immobilized on the gold. The control contains the same antibody than the test line and binds any excess of Hexon specific gold. The control line will appear in any case even if Hexon is not present indicating that the test worked correctly.

The chromatographic materials are in communication with each other in order to create a fluid pathway.

Figure 3:
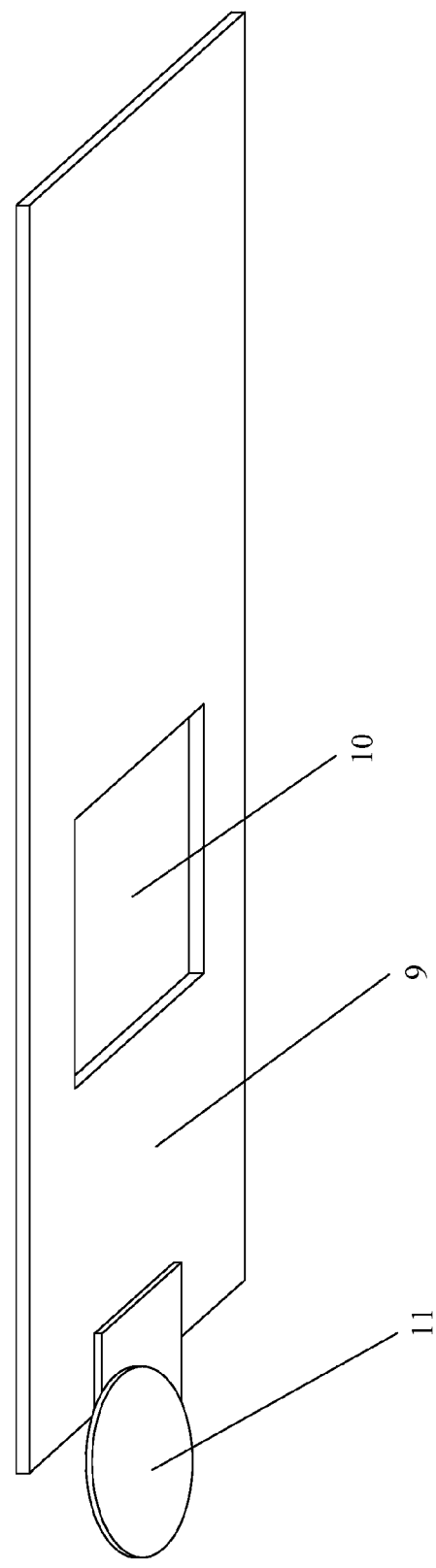
FIG. 3 shows a swab member or collection device for collecting a sample. The swab member comprises a plastic body (9) with a sample collection material (11) fixed on it and an opening (10) corresponding to a read out window when the swab member is operatively in contact with a test strip.

A sample collection device is depicted in FIG. 3. The sample collection material may consist of bibulous material such as highly purified cotton fibers which are fixed to the plastic device by ultrasonic welding. Alternative materials may be polyester, rayon, polyamide or other fibrous polymeric materials.

A test kit for the detection of Adenovirus antigen (as described in the example above) was used in the Emergency Room of an Opthalmologic Hospital to diagnose the clinical picture of a "pink" eye. From every patient which has been tested with the test kit, a second sample was taken and analysed in the laboratory.

The laboratory reference method used in this study was a combination of cell culture and immunfluorescence (IF) detection (Rodrigues et al., Opthalmology, 1979 March; 86(3):452-64) which is the current "laboratory gold standard" for determining the presence of adenovirus in human ocular fluid.

Within the testing period the following results have been achieved:

|  |  | Cell Culture/IF | |
|---|---|---|---|
|  |  | + | − |
| Adeno test kit | + | 5 | 2 |
|  | − | 0 | 21 |

These preliminary results are equivalent to a diagnostic sensitivity of 100% and a diagnostic specificity of 91%. These values are superior to diagnostic characteristics of other state of the art point-of-care devices.

The invention claimed is:

1. A method for the detection of a target which is selected from pathogens and/or allergy-associated components in a body fluid comprising the steps of:
   (a) non-invasively collecting a body fluid sample with a swab member;
   (b) directly contacting said swab member with a sample application zone on a lateral flow chromatographic test strip;
   wherein the sample is not diluted before contact between the swab member and the sample application zone on the lateral flow chromatographic test strip; and
   wherein at least a part of said body fluid sample is released directly into said sample application zone due to said swab member contacting said sample application zone;
   wherein the lateral flow chromatographic test strip further comprises a conjugate zone that is located at least partially within the sample application zone and comprises at least one binding partner for the target;
   (c) applying an elution medium to an absorbent pad on the lateral flow chromatographic test strip to transfer said sample to a detection zone on the lateral flow chromatographic test strip; and
   (d) analyzing the sample.

2. The method of claim 1 wherein the pathogen is selected from viruses, bacterium, microorganisms and parasites.

3. The method of claim 1 wherein the allergy-associated component is selected from allergens and anti-allergens.

4. The method of claim 1 wherein the body fluid is fluid from a body surface selected from mucous membrane fluids, secretions from glands and secretions from lesions or blisters.

5. The method of claim 4 wherein the sample is selected from oral, nasal, ocular, genital, and rectal fluids, and secretions from skin lesions or blisters.

6. The method of claim 5 wherein the sample is an eye fluid.

7. The method of claim 1 wherein the target is a pathogen which is a causative agent of conjunctivitis or a plurality of such causative agents.

8. The method of claim 1 wherein the pathogen is selected from the group consisting of adenoviruses, herpesviruses, chlamydiae, cytomegaloviruses, pseudomonas, streptococci, haemophilus, staphylococci, amoebae and combinations thereof.

9. The method of claim 1 wherein the target is an allergy-associated component which is a causative agent or a mediator of conjunctivitis or a plurality of such causative agents and/or mediators.

10. The method of claim 1, wherein the target comprises at least one pathogen and at least one allergy-associated component.

11. The method of claim 1 wherein the sample is about 0.1 µl to about 100 µl.

12. The method of claim 11 wherein the sample is about 0.5 µl to about 10 µl.

13. The method of claim 1 wherein step (a) comprises the substep of wiping or dabbing the swab member over a surface of a body part containing the body fluid to be tested.

14. The method of claim 1 wherein the swab member is sterile.

15. The method of claim 1 wherein the swab member is a part separate from the lateral flow chromatographic test strip.

16. The method of claim 1 further comprising the step of fixing the swab member in a contact position with the lateral flow chromatographic test strip.

17. The method of claim 1 wherein the elution medium is selected from the group consisting of a buffer or water.

18. The method of claim 1 wherein the elution medium is added from an external source or is provided within the lateral flow chromatographic test strip.

19. A method of claim 1 wherein step (d) comprises an immunological or enzymatic detection.

20. The method of claim 1, wherein the binding partner in the conjugate zone comprises at least one labeled binding partner that is able to migrate with the elution medium.

21. A method for the detection of a target which is selected from pathogens and/or allergy-associated components in a body fluid comprising the steps of:
   a) non-invasively collecting a body fluid sample with a swab member;
   b) directly contacting said swab member and said sample on said swab member with a sample application zone on a lateral flow chromatographic test strip, wherein dilution of the sample does not occur before direct contact between the swab member and the sample and the sample application zone on the lateral flow chromatographic test strip;
   c) applying an elution medium to an absorbent pad on said lateral flow chromatographic test strip to transfer said sample to a detection zone on the chromatographic test strip; and
   d) analyzing the sample;
   wherein the lateral flow chromatographic test strip further comprises a conjugate zone located at least partially within the sample application zone, wherein said conjugate zone comprises at least one labeled binding partner that is able to migrate with the elution medium wherein, when the analyte is present, the labeled binding partner complexes with the analyte and then migrates to the detection zone.

22. The method of claim 21, wherein at least a part of said body fluid sample is released directly into said sample application zone due to said swab member contacting said sample application zone.

23. The method of claim 21, wherein the body fluid sample is an eye fluid sample.

24. The method of claim 21, wherein the target is a pathogen which is a causative agent of conjunctivitis or a plurality of such causative agents.

25. A method for the detection of a target which is selected from pathogens and/or allergy-associated components in a body fluid comprising the steps of:
   a) non-invasively collecting a body fluid sample with a swab member;
   b) directly contacting said swab member with a sample application zone on a lateral flow chromatographic test strip, wherein at least a part of said body fluid sample is released directly into said sample application zone due to said swab member contacting said sample application zone; and
   wherein the lateral flow chromatographic test strip further comprises a conjugate zone that is located at least partially within the sample application zone and comprises at least one labeled binding partner for the target; and
   c) applying an elution medium to an absorbent pad on the lateral flow chromatographic test strip to transfer said sample to a detection zone on the lateral flow chromatographic test strip;
   wherein the sample is not diluted prior to steps b) and c); and
   d) analyzing the sample.

26. A method for the detection of a target which is selected from pathogens and/or allergy-associated components in a body fluid comprising the steps of:
   a) non-invasively collecting a body fluid sample with a swab member;
   b) directly contacting said swab member and said sample on said swab member with a sample application zone on a lateral flow chromatographic test strip; and
   wherein the lateral flow chromatographic test strip further comprises a conjugate zone that is located at least partially within the sample application zone and comprises at least one labeled binding partner for the target;
   c) applying an elution medium to an absorbent pad on the lateral flow chromatographic test strip to transfer said sample to a detection zone;
   wherein the sample is not diluted prior to steps b) and c); and
   d) analyzing the sample.

27. A method for the detection of a target which is selected from pathogens and/or allergy-associated components in a body fluid comprising the steps of:
   a) non-invasively collecting a body fluid sample with a swab member;
   b) directly contacting said swab member and said sample on said swab member with a sample application zone on a lateral flow chromatographic test strip, wherein dilution of the sample does not occur before direct contact between the swab member and the sample and the sample application zone on the lateral flow chromatographic test strip;
   c) applying an elution medium to an absorbent pad on said lateral flow chromatographic test strip to transfer said sample to a detection zone on the chromatographic test strip; and
   d) analyzing the sample;
   wherein the lateral flow chromatographic test strip further comprises a conjugate zone located within the sample application zone, wherein the conjugate zone comprises at least one labeled binding partner that is able to migrate with the elution medium, and wherein, when the analyte is present, the labeled binding partner complexes with the analyte and then migrates to the detection zone.

* * * * *